United States Patent
Norris et al.

(10) Patent No.: US 8,017,768 B1
(45) Date of Patent: Sep. 13, 2011

(54) CATALITIC SYNTHESIS OF CAGED POLYNITRAMINE COMPOUNDS

(75) Inventors: William P. Norris, Ridgecrest, CA (US); Arnold T. Nielsen, Santa Barbara, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 08/243,318

(22) Filed: Apr. 5, 1994

Related U.S. Application Data

(62) Division of application No. 07/466,715, filed on Sep. 1, 1990.

(51) Int. Cl.
| | |
|---|---|
| *D03D 23/00* | (2006.01) |
| *D03D 43/00* | (2006.01) |
| *F42B 15/34* | (2006.01) |
| *C07D 255/00* | (2006.01) |
| *C07D 257/00* | (2006.01) |
| *C07D 259/00* | (2006.01) |

(52) U.S. Cl. ............... 540/554; 149/109.6; 102/293
(58) Field of Classification Search ............... 540/554; 585/266, 353, 940; 149/109.6; 102/293
See application file for complete search history.

(56) References Cited

U.S. PATENT DOCUMENTS

| | | | | | |
|---|---|---|---|---|---|
| 3,228,929 | A | * | 1/1966 | Frankel | 540/554 |
| 3,941,812 | A | * | 3/1976 | Gilbert | 549/348 |
| 5,693,794 | A | * | 12/1997 | Nielsen | 540/554 |

* cited by examiner

*Primary Examiner* — Jerry Lorengo
*Assistant Examiner* — James E McDonough
(74) *Attorney, Agent, or Firm* — Melvin J. Sliwka; Brian F. Drazich; Charlene A. Haley

(57) ABSTRACT

An improved method of preparing 2,4,6,8,10,12-hexanitro-2,4,6,8,10,12-hexaazaisowurtzitane (2,4,6,8,10,12-hexanitro-2,4,6,8,10,12-hexaazatetracyclo[5.5.0.0$^{5,9}$.0$^{3,11}$]dodecane) (HNIW) is disclosed. The compound is useful as a high energy, high density explosive or propellant oxidizer.

126 Claims, No Drawings

CATALITIC SYNTHESIS OF CAGED POLYNITRAMINE COMPOUNDS

CROSS REFERENCE TO RELATED APPLICATION

This is a divisional of co pending application: Ser. No. 07/466,715 filed on 1 Sep. 1990.

This application is related to the invention entitled Caged Polynitramine Compound, filed on Sep. 30, 1988 by Arnold T. Nielsen, Ser. No. 07/253,106 and assigned to the United States of America as represented by the Secretary of the Navy, Washington, D.C.

BACKGROUND OF THE INVENTION

1. Field of the Invention

This invention relates to polyaza caged molecules having the hexaazaisowurtzitane caged ring system, including one with nitro groups attached to each nitrogen atom, and a method for producing the same, useful as an explosive. More particularly, the invention relates to an improved method of debenzylating 4,10-dibenzyl-2,6,8,12-tetraacetyl-2,4,6,8,10,12-hexaazaisowurtzitane derivative and the subsequent nitrolysis thereof to produce 2,4,6,8,10,12-hexanitro-2,4,6,8,10,12-hexaazaisowurtzitane (HNIW).

2. Description of the Related Art

Known polynitramines such as 1,3,5-trinitro-1,3,5-hexahydrotriazine (RDX) and 1,3,5,7-tetranitro-1,3,5,7-tetraazacyclooctane (HMX) are high-energy, high-density explosive compounds (R. Meyer, "Explosives," Third edition, VCH Publishers, Weinheim, Germany, 1987). They can be prepared by nitrolysis of hexamine with nitric acid and other similar procedures. Stable polynitramines having energy and density greater than that of HMX were unknown until the synthesis of a new class of explosives described as caged polynitramine was disclosed in the application by Arnold T. Nielsen on Sep. 30, 1988.

Nielsen started with benzylamine and glyoxal which are condensed in a suitable solvent in the presence of a catalyst to produce hexabenzylhexaazaisowurtzitane (HBIW). The hexabenzylhexaazaisowurtzitane (HBIW) was reductively acylated in the presence of a catalyst in a second step to produce dibenzyltetraacetylhexaazaisowurtzitane (TAIW).

The Nielsen method involved treating 4,10-dibenzyl-2,6,8,12-tetraacetyl-2,4,6,8,10,12-hexaazaisowurtzitane (TAIW) with nitrosonium tetrafluoroborate in sulfolane to form 4,10-dinitroso-2,6,8,12-tetraacetyl-2,4,6,8,10,12-hexaazaisowurtzitane (TAIW(NO)$_2$). The 4,10-dinitroso-2,6,8,12-tetraacetyl-2,4,6,8,-10,12-hexaazaisowurtzitane (TAIW(NO)$_2$) in turn was treated with nitronium tetrafluoroborate in sulfolane to give the explosive, 2,4,6,8,10,12-hexanitro-2,4,6,8,10,12-hexaazaisowurtzitane (HNIW). These flouroborate reagents are very expensive and, additionally, disposal of left-over waste is very costly because of the presence of fluoride.

SUMMARY OF THE INVENTION

This invention simplifies and greatly reduces the cost of preparation of 4,10-dinitroso-2,6,8,12-tetraacetyl-2,4,6,8,10,12-hexaazaisowurtzitane (4,10-dinitroso-2,6,8,12-tetraacetyl-2,4,6,8,10,12-hexaazatetracyclo[5.5.0.0$^{5,9}$.0$^{3,11}$] dodecane) (TAIW(NO)$_2$) and its nitrolysis to the high energy compound, 2,4,6,8,10,12-hexanitro-2,4,6,8,10,12-hexaazaisowurtzitane (2,4,6,8,10,12-hexanitro-2,4,6,8,10,12-hexaazatetracyclo[5.5.0.0$^{5,9}$.0$^{3,11}$] dodecane) (HNIW).

According to this invention, 2,4,6,8,10,12-hexanitro-2,4,6,8,10,12-hexaazaisowurtzitane (HNIW) is prepared starting with benzylamine and glyoxal which are condensed in a suitable solvent in the presence of a catalyst to produce hexabenzylhexaazaisowurtzitane (HBIW).

In the second step hexabenzylhexaazaisowurtzitane (HBIW) is reductively acylated in the presence of a catalyst to produce dibenzyltetraacetylhexaazaisowurtzitane (TAIW).

In the third step applicant diverges from Nielsen and discloses that dibenzyltetraacetylhexaazaisowurtzitane (TAIW) is debenzylated and nitrosated to produce 4,10-dinitroso-2,6,8,12-tetraacetyl-2,4,6,8,10,12-hexaazaisowurtzitane (TAIW (NO)$_2$) with dinitrogen tetraoxide.

In the last step the applicant discloses how dinitrosotetraacetylhexaazaisowurtzitane (TAIW(NO)$_2$) is nitrolyzed with a mixture of nitric acid and sulfuric acid or other nitrating mixture to give hexanitrohexaazaisowurtzitane (HNIW) in high yield.

DESCRIPTION OF THE PREFERRED EMBODIMENT

The synthesis of the first isolated intermediate compound, hexabenzylhexaazaisowurtzitane (HBIW), involves condensation of benzylamine with glyoxal (40% aqueous solution) in aqueous acetonitrile or alcohols having 1 to 4 carbon atoms (selected from the group consisting of methanol, ethanol, propanol and butanol) or a mixture of acetonitrile and such alcohols, with formic acid catalyst at 0° to 25° C. The best yield obtained (81%) requires slow addition of the aqueous glyoxal (1.0 mole-equivalent) to a solution of benzylamine (slightly more than 2 mole-equivalents) and formic acid (slightly more than 0.2 mole-equivalent) in aqueous acetonitrile, while keeping the temperature at 0° to 25° C. The optimum addition time for the glyoxal under these conditions is about one hour. After addition of all the glyoxal solution is complete, the reaction mixture is allowed to stand at ambient temperature (25° C.) overnight (16 to 18 hours) to complete the formation of the product which rapidly precipitates from the reaction mixture in rather pure form. The reaction to form hexabenzylhexaazaisowurtzitane (HBIW) is virtually over within a few hours. Prolonged standing may produce slightly higher yields without altering the purity of the product. The hexabenzylhexaazaisowurtzitane (HBIW) is isolated by suction filtration, followed by washing with cold acetonitrile or methanol and drying in air. The yields of the unrecrystallized product are 80 to 81%. The crude product is recrystallized from boiling acetonitrile to produce colorless crystals (90% recovery) with a melting point of 153° to 157° C.

Organic acid catalysts other than formic acid may be employed, such as acetic acid, or other carboxylic acid of two or more carbon atoms; the yield is decreased if more or less than 0.1 mole-equivalent of formic acid (relative to one mole-equivalent of amine) is employed. The reaction time is accelerated by heating, but yields of hexabenzylhexaazaisowurtzitane (HBIW) are not increased; excessive heating is undesirable. Solvents other than acetonitrile, such as methanol, ethanol, propanol or butanol, may be employed, but offer no advantages over acetonitrile.

The structure of hexabenzylhexaazaisowurtzitane (HBIW):

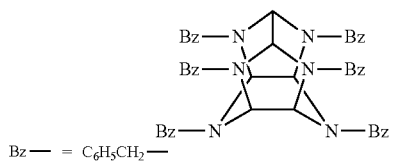

HBIW

Bz— = C₆H₅CH₂— is supported by its $^1$H and $^{13}$C NMR and mass spectra. The X-ray crystal structure of the corresponding hexa(4-methoxybenzyl)hexaazaisowurtzitane, confirms the structure of the ring system.

Several other benzylamines have been successfully condensed with glyoxal to produce substituted hexabenzylhexaazaisowurtzitanes (with comparable yields), including 4-methoxy-, 3,4-dimethoxy-, 4-methyl-, 4-isopropyl-, 2-chloro-, and 4-chlorobenzylamines.

The benzylamine may be a methylamine substituted derivative of an aromatic heterocyclic compound selected from the group consisting of thiophene, furan, pyran, pyrrole, imidazole, pyrazole, isothiazole, isoxazole, pyridine, pyrazine, indole, indolizine, quinoline, and furazan.

The second isolated intermediate compound in the reaction sequence leading to 2,4,6,8,10,12-hexanitro-2,4,6,8,10,12-hexaazaisowurtzitane (HNIW) is 4,10-dibenzyl-2,6,8,12-tetraacetyl-2,4,6,8,10,12-hexaazaisowurtzitane (TAIW).

Dibenzyltetraacetylhexaazaisowurtzitane (TAIW) is prepared by reductive acetylation of pure hexabenzylhexaazaisowurtzitane (HBIW) in an acylating agent such as acetic anhydride, or from the group of acids consisting of propionic, butyric, pentanoic and benzoic acid, with hydrogen and a hydrogenation catalyst, using a Parr shaker. For maximum yields, the reaction requires an acid promoter. Acids promoters such as sulfuric ($H_2SO_4$), hydrochloric (HCl), or hydrobromic HBr (not HI) may be added directly to the reaction mixture before hydrogenation is started. Best results have been obtained with HBr. It was found most convenient to introduce the HBr in the form of bromobenzene, acetyl bromide, benzyl bromide, or other bromine containing compounds, which are dehydrohalogenated during the hydrogenation to form the HBr. The HBr reacts with the acetic anhydride to form acetyl bromide. The concentration of HBr is critical; maximum yields were obtained at HBr concentrations of about one-eighth the number of moles of hexabenzylhexaazaisowurtzitane (HBIW).

The amount of hydrogenation catalyst, type of catalyst, and concentration of palladium on the carbon support have been varied. Palladium on charcoal is preferred over palladium metal alone. (Pd/C, 1 to 50 psi, −40° to 30° C., 2 to 24 hours). The catalyst gives best results when generated by reduction of palladium hydroxide on carbon (Pearlman's catalyst) and used in a ratio of about one-fourth the weight of hexabenzylhexaazaisowurtzitane (HBIW). Dry palladium on charcoal (3-20%) may also be used but gives lower yields (40-50%). The reaction is continued until hydrogen uptake ceases (about 6 hours), but is usually continued overnight. The solid product, dibenzyltetraacetylhexaazaisowurtzitane (TAIW), is unaffected by the prolonged reaction time. The isolation of the product involves cooling the reaction mixture to 25° C. (if an exotherm has occurred), followed by filtration of the catalyst mixed with most of the product. Some of the product remains in the acetic anhydride filtrate. The product (TAIW) (mixed with catalyst) may be recovered by extraction of the mixture with boiling chloroform, acetic acid, methylene chloride or acetonitrile. The acetic anhydride solution is concentrated under reduced pressure and the residue triturated with acetonitrile to yield the dibenzyltetraacetylhexaazaisowurtzitane (TAIW) product. The total yield of solid product is about 60-65%. The compound may be recrystallized from acetonitrile or chloroform. The crude product is quite pure and usually may be used for the next step without further purification. The structure of dibenzyltetraacetylhexaazaisowurtzitane (TAIW):

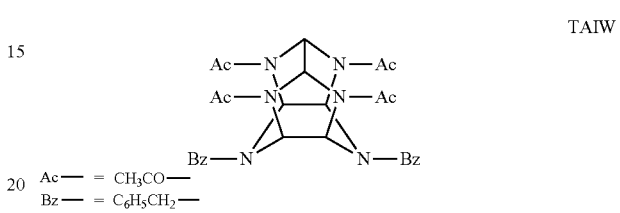

TAIW

Ac— = CH₃CO—
Bz— = C₆H₅CH₂— is supported by its $^1$H NMR, mass spectra and chemical behavior, (conversion into dinitrosotetraacetylhexaazaisowurtzitane (TAIW (NO)₂) and dinitrotetraacetylhexaazaisowurtzitane (TAIW(NO₂)₂); the X-ray crystal structure of the latter compound has been established).

The third step is substantially different from the Nielsen method in that dibenzyltetraacetylhexaazaisowurtzitane (TAIW) is debenzylated and nitrosated to produce 4,10-dinitroso-2,6,8,12-tetraacetylhexaazaisowurtzitane (TAIW (NO)₂) using dinitrogen tetraoxide (N₂O₄).

Dibenzyltetraacetylhexaazaisowurtzitane (TAIW) is added, while stirring, to dinitrogen tetraoxide (N₂O₄) in the presence of a small amount of water and cooled to 5° C. The liquid N₂O₄ turns green in color upon addition of water and the dibenzyltetraacetylhexaazaisowurtzitane (TAIW) dissolves quickly. The reaction vessel is stoppered and the solution allowed to stand, warming to ambient temperature (25° C.). A slight pressure develops in the reaction vessel due to the confined oxides of nitrogen. The reaction is allowed to stand for three (3) hours at 25° C. and then cooled to 5° C. The reaction vessel was vented to atmospheric pressure, the oxides of nitrogen evaporated, and the residue heated to 60° C. A solvent, ethanol, was then added and the mixture cooled to 5° C. with an ice bath with continuous stirring for 30 minutes. Other solvents, such as methanol, acetonitrile or methylene chloride, may be used in place of ethanol. Dinitrosotetraacetylhexaazaisowurtzitane (TAIW(NO)₂) crystals precipitated out and were filtered off. The solids were washed with more ethanol and air dried. The structure of the dinitrosotetraacetylhexaazaisowurtzitane(TAIW(NO)₂):

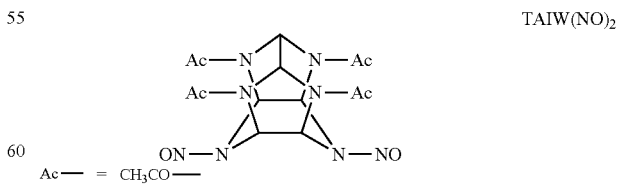

TAIW(NO)₂

Ac— = CH₃CO— is supported by x-ray crystallographic determination by R. Gilardi at the Naval Research Laboratory.

The fourth step in this invention for the improved process for making hexanitrohexaazaisowurtzitane (HNIW) is to take the dinitrosotetraacetylhexaazaisowurtzitane (TAIW(NO)$_2$) obtained above and, while stirring, add it to 99-100% nitric acid at 25° C. Then concentrated sulfuric acid is added to the mixture. The mixture is then heated to 80° to 90° C. for 2 hours and poured onto ice. A white solid, hexanitrohexaazaisowurtzitane (HNIW), precipitates out. The hexanitrohexaazaisowurtzitane (HNIW) is then washed with water and dried.

Two alternative methods may be used to produce the hexanitrohexaazaisowurtzitane (HNIW) other than as listed above. One alternative is to substitute in place of steps 3 and 4 above a "One-Pot" synthesis. The dibenzyltetraacetylhexaazaisowurtzitane (TAIW) obtained in step 2 is added to liquid dinitrogen tetraoxide ($N_2O_4$) containing a small amount of water, then cooled to 5° C. while stirring. The reaction vessel is stoppered and the mixture allowed to warm to ambient temperature (25° C.). A slight positive pressure develops due to the confined oxides of nitrogen. The reaction is allowed to stand for 3 hours at 25° C. at which time it is then cooled to 5° C. and the vessel vented to the atmosphere. Nitric acid (99-100%) and concentrated sulfuric acid are then added and the mixture heated to 80° to 90° C. for 2¼ hours. During this time the oxides of nitrogen boil off to the atmosphere. The mixture is then poured onto ice, while stirring. The hexanitrohexaazaisowurtzitane (HNIW) solid which precipitates out is washed with water and dried.

The second alternative to steps 3 and 4 above is to follow the first procedure above, (before the first alternative step), but in place of pouring the mixture onto ice to precipitate out the hexanitrohexaazaisowurtzitane (HNIW) (after heating the mixture to 80° to 90° C. for 2¼ hours), the mixture is cooled by an ice-water bath to 5° C. for 1 hour to allow the hexanitrohexaazaisowurtzitane (HNIW) solid to precipitate out. The hexanitrohexaazaisowurtzitane (HNIW) is then filtered off, washed with water and dried.

Additionally, the filtrate, fortified with nitric acid, can be used for nitrolysis of more dinitrosotetraacetylhexaazaisowurtzitane (TAIW) to yield more hexanitrohexaazaisowurtzitane (HNIW), when cooled to 5° C. and filtered. The resulting filtrate can also be used for further nitrolysis.

In addition to those nitrolysis media listed above, i.e., 99-100% nitric acid with concentrated sulfuric acid, the following nitrolysis mixtures give equally good yields: 70% nitric acid with concentrated sulfuric acid; 90% nitric acid with concentrated sulfuric acid; 100% nitric acid with 30% oleum; and 15% dinitrogen pentaoxide ($N_2O_5$) in nitric acid plus triflic acid.

The structure of 2,4,6,8,10,12-hexanitro-2,4,6,8,10,12-hexaazaisowurtzitane (HNIW):

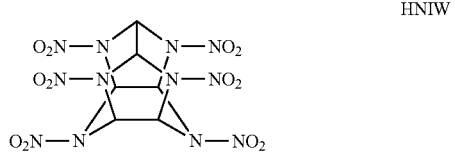

HNIW is supported by its $^1$H NMR spectrum and established by X-ray crystallography. Hexanitrohexaazaisowurtzitane (HNIW) obtained by pouring the nitrolysis mixture onto ice contains one-half molecule of water of crystallization per molecule of hexanitrohexaazaisowurtzitane(HNIW), i.e., the hemihydrate.

The compound, 2,4,6,8,10,12-hexanitro-2,4,6,8,10,12-hexaazaisowurtzitane (HNIW), may be prepared by carrying out the four-step procedure set forth in the following example.

EXAMPLE

Step 1

Preparation of 2,4,6,8,10,12-hexabenzyl-2,4,6,8,10,12-hexaazatetracyclo[5.5.0.0$^{5,9}$.0$^{3,11}$]dodecane (2,4,6,8,10,12-hexabenzyl-2,4,6,8,10,12-hexaazaisowurtzitane) (HBIW).

Glyoxal (72.5 g of 40% aqueous solution, 0.50 mole) was added drop-wise to a solution of benzylamine (117.9 g, 1.10 mole), water (100 ml), and formic acid (88%, 5.76 g, 0.110 mole) in acetonitrile (1100 ml) during one hour, keeping the temperature below 20° C. The addition funnel was rinsed with 10 ml of water. After standing at 25° C. overnight (16-18 hours), the precipitated product was removed by filtration and washed with cold acetonitrile; yield 96.0 g (81.3%) of 2,4,6,8,10,12-hexabenzyl-2,4,6,8,10,12-hexaazaisowurtzitane (HBIW); mp 150° to 152° C. Recrystallization from acetonitrile yielded a product (90% recovery of colorless prisms) with a melting point of 153° to 157° C.; IR (KBr) shows absence of NH, C=O; CH bands are found at 2949, 2830, 2750 cm$^{-1}$; $^1$H NMR (CDCl$_3$); (IBMMR-80); delta 7.20 to 7.24 (m, 30 H, phenyl CH), 4.16 (s, 4 H, CH$_2$), 4.09 (s, 8 H, CH$_2$), 4.03 (s, 4 H, CH), 3.59 (s, 2, H, CH) ppm; $^{13}$C NMR (acetone-d$_6$) (IBMNR-80): delta 141.34, 129.67, 128.82, 128.51, 127.11 (phenyl carbons), 80.94, 77.53 (1:2 intensity ratio, C of caged ring), 57.29, 56.62 (1:2 ratio, exocyclic benzyl carbons; assignments confirmed by uncoupled spectra) ppm; mass spectrum (CI, CH$_4$) m/e 709 (MH$^+$, 0.6), 618 (0.7), 473 (0.7), 237 (100); EI 91 (100). Analysis calculated for C$_{48}$H$_{48}$N$_6$: C, 81.32; H, 6.83; N, 11.86. Found C, 81.49; H, 6.91; N, 11.84.

Step 2

Preparation of 4,10-dibenzyl-2,6,8,12-tetraacetyl-2,4,6,8,10,12-hexaazaisowurtzitane (4,10-dibenzyl-2,6,8,12-tetraacetyl-2,4,6,8,10,12-hexaazatetracyclo[5.5.0.0$^{5,9}$.0$^{3,11}$]dodecane (TAIW).

A mixture of pure 2,4,6,8,10,12-hexabenzyl-2,4,6,8,10,12-hexaazaisowurtzitane (HBIW) (150 g, 0.212 mole), acetic anhydride (500 ml., 5.3 moles), Pearlman's palladium hydroxide on charcoal catalyst (37.5 g containing 20% palladium on a dry-weight basis) and bromobenzene (4.2 g, 26.5 millimole) was shaken in a 2.5-liter bottle in a Parr apparatus (50 psi, 10°-30° C., 18 hours). After cooling to 25° C. the catalyst, mixed with product, was removed by filtration and extracted with two or three 2-liter portions of boiling chloroform. Concentration of the chloroform extract yielded crude dibenzyltetraacetylhexaazaisowurtzitane (TAIW), which was triturated with acetonitrile and filtered to yield pure dibenzyltetraacetylhexaazaisowurtzitane (TAIW). The acetic anhydride filtrate was concentrated under reduced pressure, at a temperature range of 30°-70° C., to remove volatiles; the residue was triturated with acetonitrile to yield more dibenzyltetraacetylhexaazaisowurtzitane (TAIW). The combined yield was 69.0 g (63.2%) of the solid dibenzyltetraacetylhexaazaisowurtzitane (TAIW) compound with a melting point of 315° to 325° C. Recrystallization from acetonitrile yielded small colorless prisms with a melting point of 322° to 323° C.; $^1$H NMR (DMSO-d$_6$) delta 7.38, 7.31 (m, 10 H, C$_6$H$_5$), 6.50 (broad s, 2 H, CH), 5.43 (broad s, 4 H, CH), 4.07 (s, 4 H, CH$_2$), 2.03 (broad m, 12 H, CH$_3$); mass spectra (CI, CH$_4$), m/e 517 (MH$_+$. 100) 518 (32). 545 (M+29, 18), 476 (5), 455 (11), 363 (10), 111 (21). Analysis calculated for $C_{28}H_{32}N_6O_4$: C, 65.10; H, 6.24; N, 16.27. Found: C, 65.18; H, 6.50; N, 16.03.

Step 3

Preparation of 4,10-dinitroso-2,6,8,12-tetraacetyl-2,4,6,8,10,12-hexaazaisowurtzitane. (TAIW(NO)$_2$)

Five grams (0.00968 mol) of 4,10-dibenzyl-2,6,8,12-tetraacetyl-2,4,6,8,10,12-hexaazaisowurtzitane (TAIW) was added with stirring, to 25 ml of liquid dinitrogen tetraoxide ($N_2O_4$) containing 1.00 ml $H_2O$ and the mixture cooled in an ice-water bath to 5° C. The solid dissolved immediately. The reaction vessel was securely stoppered and allowed to warm to ambient temperature (25° C.). A slight positive pressure developed in the reaction vessel due to the confined oxides of nitrogen. After standing 3 hours at 25° C. the reaction mixture was cooled by an ice-water bath to 5° C., the vessel vented to atmospheric pressure, the oxides of nitrogen evaporated and the residue was heated to 60° C. Fifty (50) ml of ethanol (EtOH) was added and the mixture reheated to 60° C. and then cooled to 5° C. with stirring for 30 minutes. The solids that were formed were filtered off, washed with about 10 ml of EtOH and air dried to give 2.96 g (77.5% yield) of 4,10-dinitroso-2,6,8,12-tetraacetyl-2,4,6,8,10,12-hexaazaisowurtzitane (TAIW(NO)$_2$), with a melting point of 272° C. (with decomposition).

Step 4

Preparation of Hexanitrohexaazaisowurtzitane (2,4,6,8,10,12-hexanitro-2,4,6,8,10,12-hexaazaisowurtzitane or 2,4,6,8,10,12-hexanitro-2,4,6,8,10,12-hexaazatetracyclo[5.5.0.0$^{5,9}$.0$^{3,11}$]dodecane) (HNIW).

One gram (0.00254 mol) of 4,10-dinitroso-2,6,8,12-tetraacetyl-2,4,6,8,10,12-hexaazaisowurtzitane (TAIW(NO)$_2$) was added, with stirring, to 20 ml of 99-100% nitric acid at 25° C. Then 4.0 ml of concentrated Sulfuric Acid ($H_2SO_4$) was added and the temperature rose to 40° C. The reaction was then heated to 80° C., for 2 hours. (The reaction mixture remained clear, no precipitate, during this time.) The reaction mixture was cooled, then poured onto ice and diluted to 175 ml with ice water. A white solid precipitate was formed. The precipitated white solid was filtered off, washed with water until acid free, and air dried to give 1.02 gm (0.00228 mol, 89.7% yield) of crude hexanitrohexaazaisowurtzitane (HNIW) hemihydrate. The crude product contains 3 to 5% of by-products.

Alternative Step 4A in Place of Steps 3 & 4 Above

One-pot Synthesis of 2,4,6,8,10,12-hexanitro-2,4,6,8,10,12-hexaazaisowurtzitane (HNIW).

To 10 ml liquid dinitrogen tetraoxide ($N_2O_4$), containing 0.05 ml of $H_2O$, cooled to 5° C. and, while stirring, 5.17 g (0.0100 mol) of 4,10-dibenzyl-2,6,8,12-tetraacetyl-2,4,6,8,10,12-hexaazaisowurtzitane (TAIW) was added. The reaction vessel was securely stoppered and allowed to warm to (25° C.). (A slight positive pressure develops due to the confined oxides of nitrogen.) After letting the reaction mixture stand for 16 hours at 25° C. it was cooled to 5° C. and the reaction vessel vented to the atmosphere. Seventy (70) ml of 99-100% nitric acid and ten (10) ml of concentrated (96% approximately) sulfuric acid were added and the reaction mixture temperature raised to 80° C. for 2.25 hours. (The oxides of nitrogen were boiled off in the process.) The reaction mixture was cooled to 20° C. and poured, with stirring, onto 250 g of ice followed by filtration, washing the solid product with $H_2O$ until acid free, and air drying to give 4.39 g (98.2% yield) of crude 2,4,6,8,10,12-hexanitro-2,4,6,8,10,12-hexaazaisowurtzitane (HNIW) hemihydrate. This product contains some occluded nitric acid in the crystals and also about 3% by-product.

Alternative Step 4B

In the previous "Step 4", (not alternative step 4), in place of pouring the reaction mixture onto ice, the mixture was cooled by ice-water bath to 5° C. for one hour with stirring and the crystalline hexanitrohexaazaisowurtzitane (HNIW), which precipitated out during that time, filtered off (75% yield).

The filtrate, fortified with 99-100% nitric acid, can be used for nitrolysis of another sample of 4,10-dinitroso-2,6,8,12-tetraacetyl-2,4,6,8,10,12-hexaazaisowurtzitane (TAIW(NO)$_2$) to give 86% yield of hexanitrohexaazaisowurtzitane (HNIW), when cooled to 5° C. and filtered. This filtrate then can be used for another nitrolysis experiment.

SUMMARY OF PROPERTIES

Appearance: alpha-modification, colorless rhombic prisms
  beta-modification, colorless needles or chunky prisms
Molecular formula: $C_6H_6N_{12}O_{12}$
Molecular weight: 438.2
Oxygen balance ($CO_2$ and $H_2O$): −11.0%
Nitrogen percentage: 38.36
Detonation velocity (calculated): 9.38 mm/micro-second
Detonation pressure (calculated): 428 Kbar
Heat of formation (observed): +228 cal/g
Melting point: 260° C. (decomposition with phase changes to gamma-modification at 185° C. and to delta-modification at 230° C.)
Density (observed): alpha-modification 1.97 g/cm$^3$ beta-modification 1.98 g/cm$^3$
Impact sensitivity ($H_{50}$) using 2.5 kg type 12 tool: 17-21 cm (alpha-or beta-modification)
Friction sensitivity: 50% point: 220 lb (beta-modification)
Electrostatic sensitivity: 10/10 no fires (0.25 Joule) (alpha-modification)

The compound, 2,4,6,8,10,12-hexanitro-2,4,6,8,10,12-hexaazaisowurtzitane (HNIW), may be utilized as an explosive in the same manner that other solid, crystalline explosive materials are used. Additionally, the compound may be used as an oxidizer in solid propellant formulations. The energy of the compound is superior to that of HMX, which has a detonation velocity of 9.1 mm/microsecond and a detonation pressure of 390 Kbar. The density of the compound is also greater than that of HMX (1.90 g/cm$^3$). The compound is very stable to heat. It does not react readily with protic solvents such as water, unlike Sorguyl (tetranitroglycoluril) or hexanitrobenzene.

Modifications and variations of the present invention are possible. It should be understood that, within the scope of the appended claims, the invention may be practiced otherwise than as specifically described.

What is claimed is:
1. A method for preparing 2,4,6,8,10,12-hexanitro-2,4,6,8,10,12-hexaazaisowurtzitane (HNIW) comprising the steps of:
(A) adding stoichiometric amounts of starting materials, a benzylamine and glyoxal (40% aqueous solution) in a first solvent to form 2,4,6,8,10,12-hexabenzyl-2,4,6,8,10,12-hexaazaisowurtzitane (HBIW);

(B) shaking said 2,4,6,8,10,12-hexabenzyl-2,4,6,8,10,12-hexaazaisowurtzitane (HBIW) and an acylating agent in a Parr apparatus with hydrogen and hydrogenation catalyst to form 4,10-dibenzyl-2,6,8,12-tetraacetyl-2,4,6,8,10,12-hexaazaisowurtzitane (TAIW);

(C) adding 4,10-dibenzyl-2,6,8,12-tetraacetyl-2,4,6,8,10,12-hexaazaisowurtzitane (TAIW) to a debenzylating and nitrosating agent;

(D) adding a second solvent to the mixture to promote crystallization of 4,10-dinitroso-2,6,8,12-tetraacetyl-hexaazaisowurtzitane (TAIW(NO)$_2$);

(E) adding said 4,10-dinitroso-2,6,8,12-tetraacetyl-hexaazaisowurtzitane (TAIW(NO)$_2$) crystals to a nitrolyzing mixture to form hexanitrohexaazaisowurtzitane (HNIW); and (F) filtering off said hexanitrohexaazaisowurtzitane (HNIW).

2. The method as recited in claim 1 wherein said benzylamine in step (A) is selected from a group of benzylamines consisting of 4-methylbenzylamine, 4-isopropylbenzylamine, benzylamine, 4-methoxybenzylamine, 3,4-dimethoxybenzylamine, 2-chlorobenzylamine, and 4-chlorobenzylamine.

3. The method as recited in claim 1 wherein said benzylamine in step (A) is a methylamine substituted derivative of an aromatic heterocyclic compound selected from the group consisting of thiophene, furan, pyran, pyrrole, imidazole, pyrazole, isothiazole, isoxazole, pyridine, pyrazine, indole, indolizine, quinoline, and furazan.

4. The method as recited in claim 1 wherein said starting materials in step (A) vary from about one part benzylamine to about one part glyoxal, to about four parts benzylamine to about one part glyoxal.

5. The method as recited in claim 1 wherein said first solvent in step (A) is aqueous acetonitrile.

6. The method as recited in claim 1 wherein said first solvent in step (A) is alcohols having 1 to 4 carbon atoms, selected from the group consisting of methanol, ethanol, propanol and butanol.

7. The method as recited in claim 1 wherein said first solvent in step (A) is any mixture of aqueous acetonitrile and alcohols having 1 to 4 carbon atoms selected from the group consisting of methanol, ethanol, propanol and butanol.

8. The method as recited in claim 1 wherein said acylating agent in step (B) is acetic anhydride.

9. The method as recited in claim 1 wherein said acylating agent in step (B) is selected from the group of acids consisting of propionic, butyric, pentanoic, and benzoic.

10. The method as recited in claim 1 wherein said hydrogenation catalyst in step (B) is palladium on charcoal.

11. The method as recited in claim 1 wherein said debenzylating and nitrosating agent used in step (C) to debenzylate and nitrosate the mixture is liquid dinitrogen tetraoxide.

12. The method as recited in claim 1 wherein said second solvent in step (D) is an alcohol selected from the group consisting of methanol and ethanol.

13. The method as recited in claim 1 wherein said second solvent in step (D) is acetonitrile.

14. The method as recited in claim 1 wherein said second solvent in step (D) is methylene chloride.

15. The method as recited in claim 1 wherein said nitrolyzing mixture in step (E) is 99-100% nitric acid and concentrated sulfuric acid.

16. The method as recited in claim 1 where the product obtained in step (F) by said filtering is washed with EtOH and air dried.

17. A method for preparing 2,4,6,8,10,12-hexanitro-2,4,6,8,10,12-hexaazaisowurtzitane (HNIW) comprising the steps of:

(A) adding stoichiometric amounts of starting materials, a benzylamine and glyoxal (40% aqueous solution) in the presence of an organic acid catalyst and a first solvent at a temperature sufficient to form 2,4,6,8,10,12-hexabenzyl-2,4,6,8,10,12-hexaazaisowurtzitane (HBIW);

(B) shaking said 2,4,6,8,10,12-hexabenzyl-2,4,6,8,10,12-hexaazaisowurtzitane (HBIW) and an acylating agent in a Parr apparatus in the presence of hydrogen and a metal hydrogenation catalyst to form 4,10-dibenzyl-2,6,8,12-tetraacetyl-2,4,6,8,10,12-hexaazaisowurtzitane (TAIW);

(C) adding 4,10-dibenzyl-2,6,8,12-tetraacetyl-2,4,6,8,10,12-hexaazaisowurtzitane (TAIW) to a debenzylating and nitrosating agent;

(D) adding a second solvent to promote crystallization of 4,10-dinitroso-2,6,8,12-tetraacetylhexaazaisowurtzitane (TAIW(NO)$_2$);

(E) adding said 4,10-dinitroso-2,6,8,12-tetraacetyl-hexaazaisowurtzitane (TAIW(NO)$_2$) crystals to a nitrolyzing mixture to form hexanitrohexaazaisowurtzitane (HNIW); and (F) filtering off said hexanitrohexaazaisowurtzitane (HNIW).

18. The method as recited in claim 17 wherein said benzylamine in step (A) is selected from a group of benzylamines consisting of 4-methylbenzylamine, 4-isopropylbenzylamine, benzylamine, 4-methoxybenzylamine, 3,4-dimethoxybenzylamine, 2-chlorobenzylamine, and 4-chlorobenzylamine.

19. The method as recited in claim 17 wherein said benzylamine in step (A) is a methylamine substituted derivative of an aromatic heterocyclic compound selected from the group consisting of thiophene, furan, pyran, pyrrole, imidazole, pyrazole, isothiazole, isoxazole, pyridine, pyrazine, indole, indolizine, quinoline, and furazan.

20. The method as recited in claim 17 wherein said starting metric amounts of said starting materials in step (A) vary from about one part benzylamine to about one part glyoxal, to about four parts benzylamine to about one part glyoxal.

21. The method as recited in claim 17 wherein said aqueous solution of glyoxal in step (A) is added to said benzylamine at a rate in the range of about 0.01 mole per hour to about 1 mole per hour for a reaction on a 1 mole scale.

22. The method as recited in claim 17 wherein said temperature in step (A) is in the range from about 0° C. to about 80° C.

23. The method as recited in claim 17 wherein said first solvent in step (A) is aqueous acetonitrile.

24. The method as recited in claim 17 wherein said first solvent in step (A) is alcohols having 1 to 4 carbon atoms, selected from the group consisting of methanol, ethanol, propanol and butanol.

25. The method as recited in claim 17 wherein said first solvent in step (A) is any mixture of aqueous acetonitrile and alcohols having 1 to 4 carbon atoms selected from the group consisting of methanol, ethanol, propanol and butanol.

26. The method as recited in claim 17 wherein said organic acid catalyst in step (A) is selected from the group of acids consisting of formic, acetic, or other carboxylic acid of two or more carbon atoms.

27. The method as recited in claim 17 wherein said acylating agent in step (B) is acetic anhydride.

28. The method as recited in claim 17 wherein said acylating agent in step (B) is selected from the group of acids consisting of propionic, butyric, pentanoic, and benzoic.

29. The method as recited in claim 17 wherein said metal hydrogenation catalyst in step (B) is palladium on charcoal prepared by reduction of palladium hydroxide on charcoal.

30. The method as recited in claim 17 wherein said dibenzyltetraacetylhexaazaisowurtzitane (TAIW) obtained in step (B) is extracted with a hot solvent selected from the group consisting of chloroform, acetic acid, methylene chloride or acetonitrile.

31. The method as recited in claim 17 wherein said debenzylating and nitrosating agent used in step (C) to debenzylate and nitrosate said mixture is liquid dinitrogen tetraoxide.

32. The method as recited in claim 17 wherein said second solvent in step (D) is selected from the alcohol group consisting of methanol and ethanol.

33. The method as recited in claim 17 wherein said second solvent in step (D) is acetonitrile.

34. The method as recited in claim 17 wherein said second solvent in step (D) is methylene chloride.

35. The method as recited in claim 17 wherein said nitrolyzing mixture in step (E) is about 84% 99-100% nitric acid and about 16% concentrated sulfuric acid.

36. The method as recited in claim 17 where the product obtained in step (F) by said filtering is washed with EtOH and air dried.

37. A method for preparing 2,4,6,8,10,12-hexanitro-2,4,6,8,10,12-hexaazaisowurtzitane (HNIW) comprising the steps of:
(A) adding stoichiometric amounts of starting materials, a benzylamine and glyoxal (40% aqueous solution) in the presence of an organic acid catalyst and a first solvent at a temperature sufficient to form 2,4,6,8,10,12-hexabenzyl-2,4,6,8,10,12-hexaazaisowurtzitane (HBIW);
(B) shaking said 2,4,6,8,10,12-hexabenzyl-2,4,6,8,10,12-hexaazaisowurtzitane (HBIW) and an acylating agent in a Parr apparatus in the presence of hydrogen and a metal hydrogenation catalyst and acid promoter to form 4,10-dibenzyl-2,6,8,12-tetraacetyl-2,4,6,8,10,12-hexaazaisowurtzitane (TAIW);
(C) adding 4,10-dibenzyl-2,6,8,12-tetraacetyl-2,4,6,8,10,12-hexaazaisowurtzitane (TAIW) to a debenzylating and nitrosating agent;
(D) adding a second solvent to promote crystallization of 4,10-dinitroso-2,6,8,12-tetraacetylhexaazaisowurtzitane (TAIW(NO)$_2$);
(E) adding said 4,10-dinitroso-2,6,8,12-tetraacetylhexaazaisowurtzitane (TAIW(NO)$_2$) crystals to a nitrolyzing mixture to form hexanitrohexaazaisowurtzitane (HNIW); and
(F) filtering off said hexanitrohexaazaisowurtzitane (HNIW).

38. The method as recited in claim 37 wherein said benzylamine in step (A) is selected from a group of benzylamines consisting of 4-methylbenzylamine, 4-isopropylbenzylamine, benzylamine, 4-methoxybenzylamine, 3,4-dimethoxybenzylamine, 2-chlorobenzylamine, and 4-chlorobenzylamine.

39. The method as recited in claim 37 wherein said benzylamine in step (A) is a methylamine substituted derivative of an aromatic heterocyclic compound selected from the group consisting of thiophene, furan, pyran, pyrrole, imidazole, pyrazole, isothiazole, isoxazole, pyridine, pyrazine, indole, indolizine, quinoline, and furazan.

40. The method as recited in claim 37 wherein said starting materials in step (A) vary from about one part benzylamine to about one part glyoxal, to about four parts benzylamine to about one part glyoxal.

41. The method as recited in claim 37 wherein said aqueous solution of glyoxal in step (A) is added to said benzylamine at a rate in the range of about 0.01 mole per hour to about 1 mole per hour for a reaction on a 1 mole scale.

42. The method as recited in claim 37 wherein said temperature in step (A) is in the range from about 0° C. to about 80° C.

43. The method as recited in claim 37 wherein said first solvent in step (A) is aqueous acetonitrile.

44. The method as recited in claim 37 wherein said first solvent in step (A) is alcohols having 1 to 4 carbon atoms, selected from the group consisting of methanol, ethanol, propanol and butanol.

45. The method as recited in claim 37 wherein said first solvent in step (A) is any mixture of aqueous acetonitrile and alcohols having 1 to 4 carbon atoms selected from the group consisting of methanol, ethanol, propanol and butanol.

46. The method as recited in claim 37 wherein said organic acid catalyst in step (A) is selected from the group of acids consisting of formic, acetic, or other carboxylic acid of two or more carbon atoms.

47. The method as recited in claim 37 wherein said acylating agent in step (B) is acetic anhydride.

48. The method as recited in claim 37 wherein said acylating agent in step (B) is selected from the group of acids consisting of propionic, butyric, pentanoic, and benzoic.

49. The method as recited in claim 37 wherein said acid promoter in step (B) is an acid selected from the group consisting of sulfuric, hydrochloric and hydrobromic acid.

50. The method as recited in claim 37 wherein said acid promoter in step (B) is selected from the bromine group consisting of bromobenzene, benzyl bromide, acetyl bromide, or other easily hydrogenated brominated organic compound which produces hydrobromic acid, or hydrobromic acid itself.

51. The method as recited in claim 37 wherein said metal hydrogenation catalyst in step (B) is palladium on charcoal prepared by reduction of palladium hydroxide on charcoal.

52. The method as recited in claim 37 wherein said dibenzyltetraacetylhexaazaisowurtzitane (TAIW) obtained in step (B) is extracted with a hot solvent selected from the group consisting of chloroform, acetic acid, methylene chloride or acetonitrile.

53. The method as recited in claim 37 wherein said dibenzyltetraacetylhexaazaisowurtzitane (TAIW) obtained in step (B) is filtered out of solution along with said metal catalyst.

54. The method as recited in claim 37 wherein said dibenzyltetraacetylhexaazaisowurtzitane (TAIW) filtrate obtained in step (B) is concentrated under reduced pressure and the residue triturated with acetonitrile to yield dibenzyltetraacetylhexaazaisowurtzitane (TAIW).

55. The method as recited in claim 37 wherein said debenzylating and nitrosating agent used in step (C) to debenzylate and nitrosate said mixture is liquid dinitrogen tetraoxide.

56. The method as recited in claim 37 wherein said second solvent in step (D) is an alcohol selected from the group consisting of methanol and ethanol.

57. The method as recited in claim 37 wherein said second solvent in step (D) is acetonitrile.

58. The method as recited in claim 37 wherein said second solvent in step (D) is methylene chloride.

59. The method as recited in claim 37 wherein said nitrolyzing mixture in step (E) is about 84% 99-100% nitric acid and about 16% concentrated sulfuric acid.

60. A method for preparing 2,4,6,8,10,12-hexanitro-2,4,6,8,10,12-hexaazaisowurtzitane (HNIW) comprising the steps of:
(A) adding stoichiometric amounts of starting materials, a benzylamine and glyoxal (40% aqueous solution) in the presence of an organic acid catalyst and a first solvent at a temperature sufficient to form 2,4,6,8,10,12-hexabenzyl-2,4,6,8,10,12-hexaazaisowurtzitane (HBIW);
(B) shaking said 2,4,6,8,10,12-hexabenzyl-2,4,6,8,10,12-hexaazaisowurtzitane (HBIW) and an acylating agent in a Parr apparatus in the presence of hydrogen and a metal hydrogenation catalyst and acid promoter to form 4,10-dibenzyl-2,6,8,12-tetraacetyl-2,4,6,8,10,12-hexaazaisowurtzitane (TAIW);
(C) adding 4,10-dibenzyl-2,6,8,12-tetraacetyl-2,4,6,8,10,12-hexaazaisowurtzitane (TAIW) to a debenzylating and nitrosating agent;
(D) adding the mixture to a nitrolyzing mixture to form hexanitrohexaazaisowurtzitane (HNIW); and
(E) filtering off said hexanitrohexaazaisowurtzitane (HNIW).

61. The method as recited in claim 60 wherein said benzylamine in step (A) is selected from a group of benzylamines consisting of 4-methylbenzylamine, 4-isopropylbenzylamine, benzylamine, 4-methoxybenzylamine, 3,4-dimethoxybenzylamine, 2-chlorobenzylamine, and 4-chlorobenzylamine.

62. The method as recited in claim 60 wherein said benzylamine in step (A) is a methylamine substituted derivative of an aromatic heterocyclic compound selected from the group consisting of thiophene, furan, pyran, pyrrole, imidazole, pyrazole, isothiazole, isoxazole, pyridine, pyrazine, indole, indolizine, quinoline, and furazan.

63. The method as recited in claim 61 or 62 wherein said glyoxal in step (A) is added to a solution of said benzylamine and water.

64. The method as recited in claim 60 wherein said starting materials in step (A) vary from about one part benzylamine to about one part glyoxal, to about four parts benzylamine to about one part glyoxal.

65. The method as recited in claim 60 wherein said aqueous solution of glyoxal in step (A) is added drop-wise to said benzylamine at a rate in the range of about 0.01 mole per hour to about 1 mole per hour for a reaction on a 1 mole scale.

66. The method as recited in claim 60 wherein said temperature sufficient to form 2,4,6,8,10,12-hexabenzyl-2,4,6,8,10,12-hexaazaisowurtzitane (HBIW) in step (A) during addition of said glyoxal to said benzylamine is in the range from about 0° C. to about 80° C.

67. The method as recited in claim 60 wherein the addition of glyoxal to benzylamine in step (A) takes about one hour, followed by allowing the mixture to stand at about 25° C. overnight (16-18 hours) and the product filtered and washed with acetonitrile.

68. The method as recited in claim 60 wherein said first solvent in step (A) is aqueous acetonitrile.

69. The method as recited in claim 60 wherein said first solvent in step (A) is alcohols having 1 to 4 carbon atoms, selected from the group consisting of methanol, ethanol, propanol and butanol.

70. The method as recited in claim 60 wherein said first solvent in step (A) is any mixture of aqueous acetonitrile and alcohols having 1 to 4 carbon atoms selected from the group consisting of methanol, ethanol, propanol and butanol.

71. The method as recited in claim 60 wherein said organic acid catalyst in step (A) is selected from the group of acids consisting of formic, acetic, or other carboxylic acid of two or more carbon atoms.

72. The method as recited in claim 60 wherein said acylating agent in step (B) is acetic anhydride.

73. The method as recited in claim 60 wherein said acylating agent in step (B) is selected from the group of acids consisting of propionic, butyric, pentanoic, and benzoic.

74. The method as recited in claim 60 wherein said acid promoter in step (B) is an acid selected from the group consisting of sulfuric, hydrochloric and hydrobromic acid.

75. The method as recited in claim 60 wherein said acid promoter in step (B) is selected from the bromine group consisting of bromobenzene, benzyl bromide, acetyl bromide, or other easily hydrogenated brominated organic compound which produces hydrobromic acid, or hydrobromic acid itself.

76. The method as recited in claim 60 wherein the hydrobromic acid concentration in step (B) is about one-eighth the number of moles of hexabenzylhexaazaisowurtzitane (HBIW).

77. The method as recited in claim 60 wherein said metal hydrogenation catalyst in step (B) is palladium on charcoal prepared by hydrogenation of palladium hydroxide on charcoal.

78. The method as recited in claim 60 wherein said metal hydrogenation catalyst used in step (B) is about one-forth the weight of hexabenzylhexaazaisowurtzitane (HBIW).

79. The method as recited in claim 60 wherein the reaction mixture in step (B) is cooled to about 25° C. followed by filtration.

80. The method as recited in claim 60 wherein said dibenzyltetraacetylhexaazaisowurtzitane (TAIW) obtained in step (B) is removed from the filtrate by extraction with a hot solvent selected from the group consisting of chloroform, acetic acid, methylene chloride or acetonitrile.

81. The method as recited in claim 60 wherein said dibenzyltetraacetylhexaazaisowurtzitane (TAIW) obtained in step (B) is filtered out of solution along with said metal catalyst.

82. The method as recited in claim 60 wherein said dibenzyltetraacetylhexaazaisowurtzitane (TAIW) filtrate obtained in step (B) is concentrated under reduced pressure and the residue triturated with acetonitrile to yield dibenzyltetraacetylhexaazaisowurtzitane (TAIW).

83. The method as recited in claim 60 wherein said debenzylating and nitrosating agent used in step (C) to debenzylate and nitrosate said mixture is liquid dinitrogen tetraoxide cooled to 5° C.

84. The method as recited in claim 60 wherein said dinitrogen tetraoxide in step (C) is added while stirring.

85. The method as recited in claim 60 wherein the mixture in step (C) is stoppered and allowed to stand for about sixteen hours at 25° C. and then cooled to 5° C. and the reaction vessel vented to the atmosphere.

86. The method as recited in claim 60 wherein said nitrolyzing mixture in step (D) is added and the temperature raised to about 80° C. for about 2.25 hours.

87. The method as recited in claim 60 wherein said nitrolyzing mixture in step (D) is selected from the group consisting of 99-100% nitric acid with concentrated sulfuric acid, 70% nitric acid with concentrated sulfuric acid; 90% nitric acid with concentrated sulfuric acid; 100% nitric acid with 30% oleum; and 15% dinitrogen pentaoxide ($N_2O_5$) in nitric acid plus triflic acid.

88. The method as recited in claim 60 wherein said nitrolyzing mixture in step (D) is about 84% 99-100% nitric acid and about 16% concentrated sulfuric acid.

89. The method as recited in claim 60 wherein the mixture in step (D) is cooled and poured onto ice to precipitate out the hexanitrohexaazaisowurtzitane (HNIW).

90. The method as recited in claim 60 wherein said filtrating in step (E) is followed by washing with water and then air drying.

91. A method for preparing 2,4,6,8,10,12-hexanitro-2,4,6, 8,10,12-hexaazaisowurtzitane (HNIW) comprising the steps of:
(A) adding stoichiometric amounts of starting materials, a benzylamine and glyoxal (40% aqueous solution) in the presence of an organic acid catalyst and a first solvent at a sufficient temperature to form 2,4,6,8,10,12-hexabenzyl-2,4,6,8,10,12-hexaazaisowurtzitane (HBIW);
(B) shaking said 2,4,6,8,10,12-hexabenzyl-2,4,6,8,10,12-hexaazaisowurtzitane (HBIW) and an acylating agent in a Parr apparatus in the presence of hydrogen and a metal hydrogenation catalyst and acid promoter to form 4,10-dibenzyl-2,6,8,12-tetraacetyl-2,4,6,8,10,12-hexaazaisowurtzitane (TAIW);
(C) adding 4,10-dibenzyl-2,6,8,12-tetraacetyl-2,4,6,8,10, 12-hexaazaisowurtzitane (TAIW) to a debenzylating and nitrosating agent;
(D) adding a second solvent to promote crystallization of 4,10-dinitroso-2,6,8,12-tetraacetylhexaazaisowurtzitane (TAIW(NO)$_2$);
(E) adding said 4,10-dinitroso-2,6,8,12-tetraacetylhexaazaisowurtzitane (TAIW(NO)$_2$) crystals to a nitrolyzing mixture to form hexanitrohexaazaisowurtzitane (HNIW); and
(F) filtering off said hexanitrohexaazaisowurtzitane (HNIW).

92. The method as recited in claim 91 wherein said benzylamine in step (A) is selected from a group of benzylamines consisting of 4-methylbenzylamine, 4-isopropylbenzylamine, benzylamine, 4-methoxybenzylamine, 3,4-dimethoxybenzylamine, 2-chlorobenzylamine, and 4-chlorobenzylamine.

93. The method as recited in claim 91 wherein said benzylamine in step (A) is a methylamine substituted derivative of an aromatic heterocyclic compound selected from the group consisting of thiophene, furan, pyran, pyrrole, imidazole, pyrazole, isothiazole, isoxazole, pyridine, pyrazine, indole, indolizine, quinoline, and furazan.

94. The method as recited in claim 91 wherein said starting materials in step (A) vary from about one part benzylamine to about one part glyoxal, to about four parts benzylamine to about one part glyoxal.

95. The method as recited in claim 91 wherein said aqueous solution of glyoxal in step (A) is added drop-wise to said benzylamine at a rate in the range of about 0.01 mole per hour to about 1 mole per hour for a reaction on a 1 mole scale.

96. The method as recited in claim 91 wherein said temperature sufficient to form 2,4,6,8,10,12-hexabenzyl-2,4,6,8, 10,12-hexaazaisowurtzitane (HBIW) in step (A) during addition of said glyoxal to said benzylamine is in the range from about 0° to about 80 ° C.

97. The method as recited in claim 91 wherein the addition of glyoxal to benzylamine in step (A) takes about one hour and is followed by allowing the mixture to stand at about 25° C. overnight (16-18 hours) and the product filtered and washed with acetonitrile.

98. The method as recited in claim 91 wherein said first solvent in step (A) is aqueous acetonitrile.

99. The method as recited in claim 91 wherein said first solvent in step (A) is alcohols having 1 to 4 carbon atoms, selected from the group consisting of methanol, ethanol, propanol and butanol.

100. The method as recited in claim 91 wherein said first solvent in step (A) is any mixture of aqueous acetonitrile and alcohols having 1 to 4 carbon atoms selected from the group consisting of methanol, ethanol, propanol and butanol.

101. The method as recited in claim 91 wherein said organic acid catalyst in step (A) is selected from the group of acids consisting of formic, acetic, or other carboxylic acid of two or more carbon atoms.

102. The method as recited in claim 91 wherein said acylating agent in step (B) is acetic anhydride.

103. The method as recited in claim 91 wherein said acylating agent in step (B) is selected from the group of acids consisting of propionic, butyric, pentanoic, and benzoic.

104. The method as recited in claim 91 wherein said acid promoter in step (B) is an acid selected from the group consisting of sulfuric, hydrochloric and hydrobromic acid.

105. The method as recited in claim 91 wherein said acid promoter in step (B) is selected from the bromine group consisting of bromobenzene, benzyl bromide, acetyl bromide, or other easily hydrogenated brominated organic compound which produces hydrobromic acid, or hydrobromic acid itself.

106. The method as recited in claim 91 wherein said acid promoter concentration in step (B) is about one-eighth the number of moles of hexabenzylhexaazaisowurtzitane (HBIW).

107. The method as recited in claim 91 wherein said metal hydrogenation catalyst in step (B) is palladium on charcoal prepared by hydrogenation of palladium hydroxide on charcoal.

108. The method as recited in claim 91 wherein said metal hydrogenation catalyst used in step (B) is about one-forth the weight of hexabenzylhexaazaisowurtzitane (HBIW).

109. The method as recited in claim 91 wherein the reaction mixture in step (B) is cooled to about 25° C. followed by filtration.

110. The method as recited in claim 91 wherein said dibenzyltetraacetylhexaazaisowurtzitane (TAIW) obtained in step (B) is extracted with a hot solvent selected from the group consisting of chloroform, acetic acid, methylene chloride or acetonitrile.

111. The method as recited in claim 91 wherein said dibenzyltetraacetylhexaazaisowurtzitane (TAIW) obtained in step (B) is filtered out of solution along with said metal catalyst.

112. The method as recited in claim 91 wherein said dibenzyltetraacetylhexaazaisowurtzitane (TAIW) filtrate obtained in step (B) is concentrated under reduced pressure and the residue triturated with acetonitrile to yield dibenzyltetraacetylhexaazaisowurtzitane (TAIW).

113. The method as recited in claim 91 wherein said debenzylating and nitrosating agent used in step (C) to debenzylate and nitrosate said mixture is liquid dinitrogen tetraoxide.

114. The method as recited in claim 91 wherein said dinitrogen tetraoxide is added in step (C) while stirring in the presence of a small amount of water cooled to 5° C.

115. The method as recited in claim 91 wherein the mixture in step (C) is stoppered and allowed to stand, warming to ambient temperature (about 25° C.) for three hours and then cooled to 5° C.

116. The method as recited in claim 91 wherein the reaction vessel in step (C) is vented to atmospheric pressure and heated to about 60° C.

117. The method as recited in claim 91 wherein said second solvent in step (D) is selected from an alcohol group consisting of methanol and ethanol.

118. The method as recited in claim 91 wherein said second solvent in step (D) is acetonitrile.

119. The method as recited in claim 91 wherein said second solvent in step (D) is methylene chloride.

120. The method as recited in claim 91 wherein after said second solvent in step (D) is added the mixture is cooled to 5° C. with continuous stirring and the dinitrosotetraacetylhexaazaisowurtzitane (TAIW $(NO)_2$) filtered off.

121. The method as recited in claim 91 wherein said nitrolyzing mixture in step (E) is selected from the group consisting of 99-100% nitric acid with concentrated sulfuric acid, 70% nitric acid with concentrated sulfuric acid; 90% nitric acid with concentrated sulfuric acid; 100% nitric acid with 30% oleum; and 15% dinitrogen pentaoxide ($N_2O_5$) in nitric acid plus triflic acid.

122. The method as recited in claim 91 wherein said nitrolyzing mixture in step (E) is about 84% 99-100% nitric acid and about 16% concentrated sulfuric acid.

123. The method as recited in claim 91 wherein said dinitrosotetraacetylhexaazaisowurtzitane (TAIW $(NO)_2$) is added to nitric acid and sulfuric acid in step (E) and the mixture heated to about 80° C. for about 2 hours.

124. The method as recited in claim 91 wherein the mixture in step (E) is cooled and then poured onto ice and diluted with water to precipitate out the hexanitrohexaazaisowurtzitane (HNIW).

125. The method as recited in claim 91 wherein the mixture in step (E) is cooled by an ice-water bath to about 5° C. for about 1 hour to allow the hexanitrohexaazaisowurtzitane to precipitate out.

126. The method as recited in claim 91 wherein said filtrating in step (F) is followed by washing with water until the product is acid free and then air dried.

* * * * *